(12) United States Patent
Unhoch et al.

(10) Patent No.: US 7,008,531 B2
(45) Date of Patent: Mar. 7, 2006

(54) TREATMENT OF CIRCULATING WATER SYSTEMS

(75) Inventors: Michael Joseph Unhoch, Newcastle, DE (US); Roy Dean Vore, Newcastle, DE (US)

(73) Assignee: Arch Chemicals Inc., Norwalk, CT (US)

( * ) Notice: Subject to any disclaimer, the term of this patent is extended or adjusted under 35 U.S.C. 154(b) by 52 days.

(21) Appl. No.: 10/946,609

(22) Filed: Sep. 22, 2004

(65) Prior Publication Data

US 2005/0036982 A1   Feb. 17, 2005

Related U.S. Application Data

(62) Division of application No. 10/296,861, filed as application No. PCT/GB01/02362 on May 29, 2001, now Pat. No. 6,811,711.

(60) Provisional application No. 60/209,230, filed on Jun. 2, 2000.

(51) Int. Cl.
 *C02F 1/50* (2006.01)

(52) U.S. Cl. .................. 210/167; 210/169; 504/158; 504/159; 504/160; 514/635; 514/642; 514/667; 514/674

(58) Field of Classification Search .............. 162/161; 210/755, 764, 167, 169; 422/28; 504/158–160; 514/635, 642, 554, 556, 663, 667, 674
See application file for complete search history.

(56) References Cited

U.S. PATENT DOCUMENTS

| | | | |
|---|---|---|---|
| 2,393,293 A | 1/1946 | Corkey | 504/152 |
| 5,668,084 A | 9/1997 | Unhoch et al. | 504/158 |
| 5,779,914 A | 7/1998 | Brown et al. | 210/754 |
| 5,783,091 A | 7/1998 | Werle et al. | 210/755 |
| 5,866,016 A | 2/1999 | Jaquess et al. | 210/764 |
| 5,935,518 A | 8/1999 | Richard et al. | 422/28 |
| 6,103,666 A | 8/2000 | Del Corral et al. | 504/160 |
| 6,207,048 B1 * | 3/2001 | Bonelli | 210/198.1 |
| 6,730,654 B1 * | 5/2004 | Godfroid et al. | 510/499 |
| 6,811,711 B1 * | 11/2004 | Unhoch et al. | 210/755 |

FOREIGN PATENT DOCUMENTS

| WO | WO 97/28091 | 8/1997 |
|---|---|---|
| WO | WO 98/00369 | 1/1998 |
| WO | WO 98/52875 | 11/1998 |

OTHER PUBLICATIONS

Derwent Publications Ltd., London, GB, Class A97, AN 1998-189101, XP002186957.

* cited by examiner

*Primary Examiner*—Peter A. Hruskoci
(74) *Attorney, Agent, or Firm*—Morgan, Lewis & Bockius LLP

(57) ABSTRACT

The present invention relates to a method of inhibiting the growth of killing algae, bacteria, yeast and/or fungi in a recirculating water system which comprises adding to the water a polymeric biguanide and an adjuvant of the Formula (1) or a salt thereof:

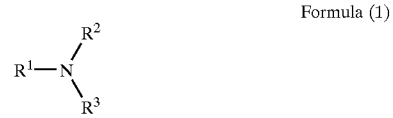

Formula (1)

wherein:
$R^1$ is an optionally substituted $C_8$ to $C_{12}$ or $C_{18}$ to $C_{22}$ alkyl group; and
$R^2$ and $R^3$ each independently is H or optionally substituted $C_{1-4}$-alkyl.

15 Claims, No Drawings

TREATMENT OF CIRCULATING WATER SYSTEMS

This application is a divisional of U.S. application Ser. No. 10/296,861 which was filed Jun. 3, 2003 now U.S. Pat. No. 6,811,711 as a Section 371 national phase filing based on PCT/GB01/02362, filed May 29, 2001, said PCT application claiming the benefit of U.S. provisional Appln. No. 60/209,230, filed Jun. 2, 2000. The present application claims the benefit of all of said earlier filings.

FIELD OF INVENTION

This invention relates to a method for inhibiting the growth of or killing microorganisms such as algae, bacteria, yeast and/or fungi in a recirculating water system, to treated recirculating water systems and to compositions and kits suitable for use in the method.

BACKGROUND OF THE INVENTION

The water in many industrial and recreational recirculating water systems such as cooling towers, swimming pools, spas, ornamental ponds, plumbing, pipework and other surfaces and the like is susceptible to infection by microorganisms such as bacteria, algae, yeast and fungi. These organisms may be pathogens or potential pathogens. Thus, for safety reasons, it is highly desirable to control their growth by the addition to the water of sanitizing agents. It is also desirable for aesthetic reasons, to control the growth of non-pathogenic bacteria, algae, yeast and fungi, particularly the so-called "nuisance" algae, yeast and fungi which cause discoloration and/or staining of the water and surfaces in contact with the water A variety of sanitising agents have been employed for controlling undesirable micro-organisms in recreational recirculating water systems. The most common sanitising agents provide free chlorine and/or bromine (typically at a concentration in the water of 1 to 5 ppm free halogen). Chlorine may be provided either directly as chlorine gas or sodium or calcium hypochlorite or via a chlorine release agent such as a chlorinated isocyanurate or chlorinated and brominated hydantoin. Chlorine may also liberated in situ by electrolysis of sodium chloride. Other sanitising agents which have been used in such systems include ozone, ozone forming chemicals, hydrogen peroxide, hydrogen peroxide forming chemicals, copper and/or silver salts which provide copper, silver or chelated copper ions (typically at a concentration in the water of 0.1 to 1.0 ppm), quaternary amines and polymeric biguanides, especially poly(hexamethylene biguanide) (hereinafter referred to as PHMB) which is typically used at a concentration in recreational water of 6–10 ppm. Systems employing ultra violet light have also been used to sanitise recirculating water. Sanitising agents are used at higher concentrations in industrial recirculating water systems and additional sanitising agents may be used including but not limited to 2-methylisothiazolinone, 5-chloro-2-methylisothiazolinone, benzisothiazolinone, 2-bromo-2-nitropropane-1,3-diol, 1,2-dibromo-2,4-dicyanobutane, methylene bisthiocyanate, 2-(thiocyanomethylthio)-benzothiazole, formaldehyde and formaldehyde release agents, glutaraldehyde, dibromonitrilopropionamide and bromo-hydroxyacetophenone or mixtures thereof.

Although these primary sanitising agents are very effective in controlling bacteria they do not always provide consistent control of the so called "nuisance" algae, yeast and fungi which can cause discoloration and/or staining of the water and surfaces in contact with the water.

Examples of "nuisance" algae which are found in swimming pools include eukaryotic and prokaryotic algae, for example green algae (e.g. *Chlorella* spp.), black algae (e.g. *Phormidium* spp.) and mustard algae (e.g. *Eustigmatos* spp.). Of these, we have found that mustard algae are particularly difficult to control, regardless of the type of primary sanitising agent used. They appear as slimy deposits attached to the pool sides and bottom, as well as in the plumbing and in the filter, and vary in colour from dark green to brown.

Examples of "nuisance" fungi (often referred to as mold) isolated from swimming pools include *Aspergillus* spp., *Cladosporium* spp., *Mucor* spp. and *Paecilomyces* spp. *Paecilomyces lilacinus* is the causative agent in so-called "water mold", "pink mold" and "pink algae". *P lilacinus* can manifest itself as white, grey or pink slimy deposits that are found in niches such as under ladder steps, in skimmer and pump baskets, in filters and piping. *P lilacinus* is also found growing in recirculating water filters where it can have an adverse effect on the efficiency and lifespan of the filter media. In its mature form, the fungus can also attach itself to pool surfaces and cause chronic turbidity problems which are difficult to control.

Examples of common "nuisance" yeasts found in swimming pools include *Saccharomyces* and *Candidia* species.

The wide spread occurrence of "nuisance" algae and fungi has lead to the introduction of methods of controlling these persistent microbes such as dosing with larger amounts of the sanitiser, shock dosing with chlorine or the introduction of further sanitisers or additives such as chelated copper, copper sulfate, combinations of chlorine and ammonium sulfate, colloidal silver, linear and/or cyclic quaternary amine compounds and polyquaternary amine compounds. However, these methods and algicides/fungicides have shown only limited efficacy against the "nuisance" algae and fungi and can give rise to undesirable levels of foam, especially in re-circulating water systems such as spas. Furthermore, in some circumstances, the additives themselves (especially chelated copper and copper sulphate) can cause staining of surfaces in contact with the water.

Any agent to be added to a recreational water system to control bacterial growth and "nuisance" algae, yeast and fungi must meet a number of demanding performance criteria. These include:
a) an excellent toxicology profile;
b) reasonable solubility;
c) freedom from unpleasant taste;
d) odourless or free from unpleasant odours (post addition);
e) non-staining of the construction materials e.g. plaster, plastic;
f) stability to light;
g) stability to other additives present in the water (e.g. sanitisers, $H_2O_2$ and EDTA);
h) little or no effect on foaming; and
i) no adverse effect on water appearance e.g. discoloration or turbidity.

Thus, there is a need for a method of treating recirculating water systems to control not only the growth of pathogens, potential pathogens and other bacteria, but also the growth of those "nuisance" algae, yeast and/or fungi which persist in the presence of a primary sanitizing agent.

SUMMARY OF THE INVENTION

According to the present invention there is provided a method for inhibiting the growth of or killing microorganisms, particularly bacteria, algae, yeast, and/or fungi in a recirculating water system comprising adding to the water a polymeric biguanide and an adjuvant of the Formula (1) or a salt thereof:

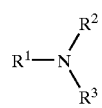

Formula (1)

wherein:
$R^1$ is an optionally substituted $C_8$ to $C_{12}$ or $C_{18}$ to $C_{22}$ alkyl group; and
$R^2$ and $R^3$ each independently is H or optionally substituted $C_{1-4}$-alkyl.

The Adjuvant

The alkyl group represented by $R^1$ may be a branched chain or more preferably a straight chain alkyl group. It is especially preferred that $R^1$ is n-octadecyl or more preferably n-dodecyl.

When any of $R^2$ and $R^3$ is $C_{1-4}$-alkyl it may be a branched chain or more preferably a straight chain alkyl group. Examples of suitable alkyl groups include ethyl, n-propyl, iso-propyl and especially methyl. It is preferred however that $R^2$ and $R^3$ are H.

The alkyl groups represented by $R^1$, $R^2$ and $R^3$ may be substituted by one or more substituents which do not adversely affect the activity of the adjuvant when used in combination with a polymeric biguanide according to the present invention. Suitable optional substituents include hydroxy, aryl (especially phenyl), amino, $C_{1-4}$-alkoxy, hydroxy-$C_{1-4}$-alkoxy or halogen (especially Cl). It is preferred, however that $R^1$, $R^2$ and $R^3$ are un-substituted.

The adjuvant is preferably sufficiently water-soluble to give a concentration thereof in the recirculating water system which is sufficient to inhibit the growth of or kill microorganisms such as bacteria, algae, yeast, and/or fungi present in the recirculating water system. When the adjuvant is added to a recreational recirculating water system such as a swimming pool or spa it is also preferable that the adjuvant has sufficient water solubility not to adversely effect the appearance of the water in the recirculating water system, for example water colour or clarity.

Preferably the adjuvant has a water-solubility of at least 1 ppm, preferably at least 2 ppm, especially at least 5 ppm more especially at least 50 ppm and particularly at least 100 ppm. The upper limit of the adjuvant's water-solubility does not matter, although typically the adjuvant has a water-solubility below 100,000 ppm, more usually below 25,000 ppm.

The term "ppm" means parts per million by weight. One may easily determine the water-solubility of an adjuvant in ppm because this is the same as the weight of adjuvant in milligrams which will dissolve in 1 litre of water at 20° C. For example if 10 mg of adjuvant dissolves in 1 litre of water at 20° C. the water-solubility is 10 ppm.

The solubility of many adjuvants is influenced by pH. In a recreational recirculating water system the pH is preferably in the range of from 6.5 to 9.0, more preferably from 6.8 to 8.5 and especially from 7.0 to 8.2. Accordingly the above mentioned preferred solubility of the adjuvant is the solubility in water at the pH of the recirculating water system.

The adjuvant is preferably added to the water system to give a concentration thereof in the range 0.1 to 30 ppm, more preferably 0.1 to 24 ppm, more preferably 0.5 to 15 ppm, especially 5 to 15 ppm and more especially 6 to 10 ppm. These preferred concentrations provide good protection against the growth of microorganisms such as bacteria and nuisance algae, yeasts and fungi. It is especially preferred that the concentration of adjuvant is less than 25 ppm, because we have found that in some circumstances a higher concentration of adjuvant can result in water turbidity.

In view of the foregoing preferences the adjuvant is preferably selected from the group consisting of dodecylamine, octadecylamine, N,N-dimethyloctadecylamine and salts thereof. It is especially preferred that the adjuvant is dodecylamine or octadecylamine or a salt thereof. More especially the adjuvant is dodecylamine or a salt thereof. Dodecylamine provides good protection against the growth of microorganisms such as bacteria and "nuisance" algae, yeast and/or fungi and does not affect water quality, particularly water clarity.

When the adjuvant is used in the form of a salt, the salt may be formed with any anion which does not adversely affect the activity of the adjuvant when used with the polymeric biguanide. Preferably, the salt is an acid addition salt, more preferably a water-soluble acid addition salt. The acid forming the salt may be an inorganic acid or an organic acid. When the acid is an inorganic acid it is preferably hydrochloric acid.

When the salt is formed with an organic acid, the acid may contain a phosphonic, phosphoric, sulphonic or sulphate group but preferably contains a carboxylic acid group. The organic acid may be aromatic but is preferably aliphatic, including alicyclic. When the organic acid is aliphatic, the aliphatic chain of the organic acid may be linear or branched, saturated or unsaturated, including mixtures thereof. Preferably, the aliphatic chain is linear and it is also preferred that the organic acid is an aliphatic carboxylic acid.

It is preferred that the organic acid contains up to 12, more preferably up to 6 carbon atoms excluding the acid group.

The organic acid may contain more than one acid group but it is preferred that only one such group is present.

The organic acid may be substituted by a halogen or particularly a hydroxy group.

Suitable aliphatic carboxylic acids from which the salt can be formed include acetic acid, propionic acid, butyric acid, valeric acid, pivalic acid and lauric acid. Suitable aliphatic di-carboxylic acids include oxalic acid, malonic acid, succininic acid and gluconic acid. Suitable hydroxy substituted acids include glycolic acid, lactic acid, glyceric acid, malic acid and tartaric acid.

The salts of the adjuvant may be formed using conventional methods, for example by reacting the compound of Formula (1) with the acid optionally in the presence of a solvent. The resulting salt may then be isolated by, for example evaporation. It is preferred that the resulting salt is purified prior to use in the present method to remove undesirable impurities.

A single adjuvant or two or more of the adjuvants may be used in the present method. The use of two or more of the adjuvants may advantageously provide a broader spectrum of activity than the use of a single adjuvant.

Polymeric Biguanide

The polymeric biguanide preferably contains at least two biguanide units of Formula (2):

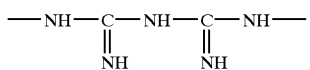

Formula (2)

linked by a bridging group which contains at least one methylene group. The bridging group preferably includes a polymethylene chain, optionally incorporating or substituted by one or more hetero atoms such as oxygen, sulphur or nitrogen. The bridging group may include one or more cyclic moieties which may be saturated or unsaturated. Preferably, the bridging group is such that there are at least three, and especially at least four, carbon atoms directly interposed between two adjacent biguanide units of Formula (2). Preferably, there are not greater than 10 and especially not greater than eight carbon atoms interposed between two adjacent biguanide units of Formula (2).

The polymeric biguanide may be terminated by any suitable group, such as a hydrocarbyl, substituted hydrocarbyl or by an amine group or by a cyanoguanidine group of the formula:

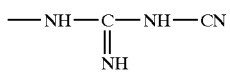

When the terminating group is hydrocarbyl, it is preferably alkyl, cycloalkyl, aryl or aralkyl. When the terminating group is substituted hydrocarbyl, the substituent may be any substituent which does not exhibit undesirable adverse effects on the microbiological properties of the polymeric biguanide. Preferred aryl groups include phenyl groups. Examples of suitable substituents are aryloxy, alkoxy, acyl, acyloxy, halogen and nitrile.

When the polymeric biguanide contains two biguanide groups of Formula (2), it is preferred that the two biguanide groups are linked through a polymethylene group, especially a hexamethylene group and the biguanide is a bisbiguanide.

The terminating groups in such bisbiguanides are preferably $C_{1-10}$-alkyl which may be linear or branched and optionally substituted aryl, especially optionally substituted phenyl. Examples of such terminating groups are 2-ethylhexyl and 4-chlorophenyl. Specific examples of such bisbiguanides are compounds represented by Formula (3) and (4) in the free base form:

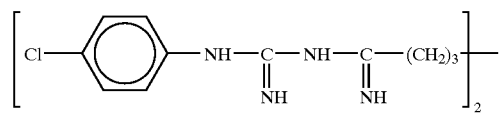

Formula (3)

and

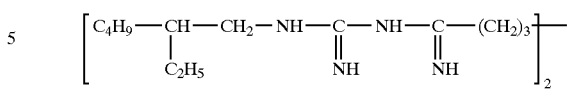

Formula (4)

The polymeric biguanide preferably contains more than two biguanide units of Formula (2) and is preferably a linear polymeric biguanide which has a recurring polymeric chain represented by Formula (5) or a salt thereof:

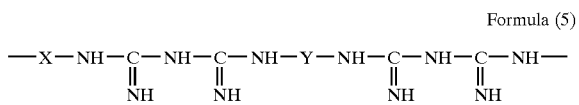

Formula (5)

wherein X and Y represent bridging groups which may be the same or different and in which together the total of the number of carbon atoms directly interposed between the pairs of nitrogen atoms linked by X plus the number of carbon atoms directly interposed between the pairs of nitrogen atoms linked by Y is more than 9 and less than 17.

The bridging groups X and Y preferably consist of polymethylene chains, optionally interrupted by hetero atoms, for example, oxygen, sulphur or nitrogen. X and Y may also incorporate cyclic moieties which may be saturated or unsaturated, in which case the number of carbon atoms directly interposed between the pairs of nitrogen atoms linked by X and Y is taken as including that segment of the cyclic group, or groups, which is the shortest. Thus, the number of carbon atoms directly interposed between the nitrogen atoms in the group

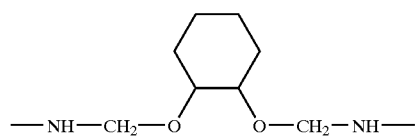

is 4 and not 8.

The linear polymeric biguanides having a recurring polymer unit of Formula (5) are typically obtained as mixtures of polymers in which the polymer chains are of different lengths. Preferably, the number of individual biguanide units of formulae:

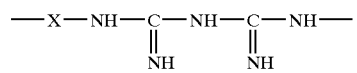

and

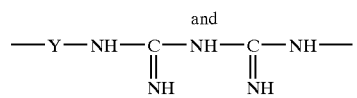

is, together, from 3 to about 80.

The preferred linear polymeric biguanide is a mixture of polymer chains in which X and Y are identical and the individual polymer chains, excluding the terminating groups, are of the Formula (6) or a salt thereof:

Formula (6)

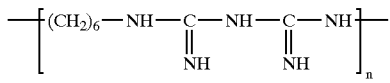

wherein n is from 4 to 40 and especially from 4 to 15. It is especially preferred that the average value of n is about 12. Preferably, the average molecular weight of the polymer in the free base form is from 1100 to 3300.

The linear polymeric biguanides may be prepared by the reaction of a bisdicyandiamide having the formula:

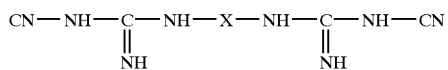

with a diamine $H_2N$—Y—$NH_2$, wherein X and Y have the meanings defined above or by reaction between a diamine salt or dicyanimide having the formula:

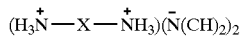

with a diamine $H_2N$—Y—$NH_2$ wherein X and Y have the meanings defined above. These methods of preparation are described in UK specifications numbers 702,268 and 1,152,243 respectively, and any of the polymeric biguanides described therein may be used.

As noted hereinbefore, the polymer chains of the linear polymeric biguanides may be terminated either by an amino group or by a cyanoguanidine group:

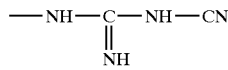

This cyanoguanidine group can hydrolyse during preparation of the linear polymeric biguanide yielding a guanidine end group. The terminating groups may be the same or different on each polymer chain.

A small proportion of a primary amine R—$NH_2$, where R represents an alkyl group containing from 1 to 18 carbon atoms, may be included with the diamine $H_2N$—Y—$NH_2$ in the preparation of polymeric biguanides as described above. The primary amine acts as a chain-terminating agent and consequently one or both ends of the polymeric biguanide polymer chains may be terminated by an —NHR group. These —NHR chain-terminated polymeric biguanides may also be used.

The polymeric biguanides readily form salts with both inorganic and organic acids. Preferred salts of the polymeric biguanide are water-soluble. When the polymeric biguanide is represented by a compound of Formula (3) in the free base form, a preferred water soluble salt is the digluconate. When the polymeric biguanide is represented by a compound of Formula (4) in the free base form, a preferred water soluble salt is the diacetate. When the polymeric biguanide is a mixture of linear polymers represented by Formula (6) in the free base form, the preferred salt is the hydrochloride.

It is especially preferred that the polymeric biguanide is a mixture of linear polymers, the individual polymer chains of which, excluding the terminating groups, are represented by Formula (6) in the hydrochloride salt form. This is commercially available from Avecia Inc. under the trademark BAQUACIL The polymeric biguanide is preferably added to the recirculating water system to give a concentration thereof in the water of from 1 to 20 ppm, more preferably from 4 to 15 ppm, especially from 5 to 12 ppm, more especially from 6 to 10 ppm.

We have found that a combination of a polymeric biguanide (especially PHMB) with an adjuvant of the Formula (1) or a salt thereof provides particularly effective control over the growth of bacteria and nuisance algae, yeast and fungi. Furthermore, the combination of the polymeric biguanide and adjuvant gives a fast rate of kill of undesirable micro-organisms. We have also found that the combination of adjuvant and polymeric biguanide exhibit a high residence time in the water, thereby providing long term protection against the growth of bacteria and nuisance algae. A long residence time is desirable because it reduces the frequency of re-dosing with the polymeric biguanide and/or adjuvant necessary to sustain protection in the recirculating water system.

As hereinbefore mentioned the polymeric biguanide and adjuvant may be added sequentially in any order. However, for ease of dosing it is preferred that they are added together as a composition comprising the polymeric biguanide, the adjuvant and optionally a carrier. The carrier, when present, may be a solid or a liquid medium and may comprise a mixture of one or more solids or liquids.

When the carrier is a solid it is preferably a solid which, when dissolved in the recirculating water system, does not have an adverse effect upon the water, such as discoloration of the water or causing turbidity. It is especially preferred that the solid is a water soluble solid, because this avoids the formation of undesirable deposits in the recirculating water system. Solid carriers which may be used include, but are not limited to kaolin, bentonite, kieselguhr, calcium carbonate, talc, powdered magnesia, china clay or more preferably a water soluble inorganic salt, or a filler conventionally used in the preparation of tablets, such as microcrystalline cellulose, lactose and mannitol.

When the carrier is a solid the adjuvant and polymeric biguanide may be simply mixed with the carrier to provide a powder formulation which can be added directly to the recirculating water system. Alternatively, the powder may be encapusulated in a water-soluble capsule, for example as is commonly used for encapsulating pharmaceuticals. This has the advantage that dosing of the powder is easily controlled, for example a single capsule can be filled with sufficient powder to give an effective concentration of the polymeric biguanide and adjuvant in the recirculating water system.

In an embodiment of the invention the polymeric biguanide and adjuvant may be used in the form of a tablet. Suitable tablet formulations include those commonly used for dispensing pharmaceuticals. The tablets may contain a number of components commonly used in the art of tablet formulation, for example, fillers, binders, and excipients.

When the carrier is a liquid medium, the composition is preferably a solution, suspension, emulsion, dispersion or micro-emulsion of the polymeric biguanide and adjuvant in the liquid medium.

The liquid medium is preferably water, a water-miscible organic solvent or more preferably a mixture of water and one or more water-miscible organic solvents.

Suitable water-miscible organic solvents include alcohols, preferably $C_{1-6}$-alkanols, for example methanol, ethanol, propanol and isopropanol; diols, preferably diols having from 2 to 12 carbon atoms, for example pentane-1,5-diol, ethylene glycol, propylene glycol, butylene glycol, pentylene glycol, hexylene glycol and thiodiglycol; oligo- and poly-alkyleneglycols, for example diethylene glycol, triethylene glycol, dipropylene glycol, polyethylene glycol (preferably with an average $M_n$<1000, more preferably <500) and polypropylene glycol (preferably with an average $M_n$<1000); triols, for example glycerol and 1,2,6-hexanetriol; mono-$C_{1-4}$-alkyl ethers of diols, preferably mono-$C_{1-4}$-alkyl ethers of diols having 2 to 12 carbon atoms, for example 2-methoxyethanol, 2-(2-methoxyethoxy)ethanol, 2-(2-ethoxyethoxy)ethanol, 2-[2-(2-methoxyethoxy)ethoxy]ethanol, 2-[2-(2-ethoxyethoxy)-ethoxy]-ethanol and ethyleneglycol monoallylether; amides, for example N,N-dimethylformamide; cyclic amides, for example N-methyl-2-pyrrolidone, N-ethyl-2-pyrrolidone and 2-pyrrolidone; and sulphoxides, for example, dimethylsulphoxide; carboxylic acids, for example saturated and unsaturated aliphatic monocarboxylic or dicarboxylic acids for example methanoic, ethanoic, propanoic, butanoic, 2-methylpropanoic, pentanoic, 3-methylbutanoic, 2,2-dimethylpropanoic, dodecanoic, tetradecanoic, hexadecanoic, octadecanoic, ethandioic, propanedioic, butanedioic, pentandioic, hexanedioic, heptanedioic, octanedioic, nonanedioic, and decanedioc acid, unsaturated aliphatic acid for example propenoic, propynoic, 2-methylpropenoic, trans and cis-2-butenoic, trans and cis-9-octadecanoic, trans and cis-butenoic and cis-methylbutenedioic, $C_{1-6}$-alkanols and $C_{1-6}$ saturated carboxylic acids are particularly preferred. Especially preferred water-miscible organic solvents include acetic acid, propanoic acid and ethanol.

If the formulation is in the form of a suspension, dispersion or emulsion, it preferably also contains a surface active agent to produce a stable dispersion or to maintain the non-continuous phase uniformly distributed throughout the continuous phase. Any surface active agent which does not have a significantly adverse effect on the biocidal activity of the adjuvant and polymeric biguanide may be used. Suitable surface active agents include emulsifiers and surfactants and mixtures thereof. The emulsifiers/surfactants may by non-ionic, anionic or a mixture thereof. Suitable anionic emulsifiers and surfactants include alkylarylsulfonates (for example calcium dodecylbenzenesulfonate), alkylsulfates (for example sodium dodecylsulfate), sulfosuccinates (for example sodium dioctylsulfosuccinate), alkylethersulfates, alkylarylethersulfates, alkylether carboxylates, alkylarylethercarboxylates, lignin sulfonates or phosphate esters. Suitable non-ionic emulsifiers and surfactants include fatty acid ethoxylates, ester ethoxylates, glyceride ethoxylates (for example castor oil ethoxylate), alkylaryl polyglycol ethers (for example nonylphenol ethoxylates), alcohol ethoxylates, propylene oxide-ethylene oxide condensation products, amine ethoxylates, amide ethoxylates, amine oxides, alkyl polyglucosides, sorbitan fatty acid esters, polyoxyethylene sorbitan fatty acid esters, polyoxyethylenesorbitol esters or alcohol ethoxy carboxylates, especially those obtainable from $C_{12-14}$-alcohols.

The weight ratio of the polymeric biguanide:adjuvant may vary over wide limits, but in many embodiments is from 99:1 to 1:99, preferably from 4:1 to 1:4, more preferably from 1:2 to 2:1. It is especially preferred that the weight ratio of the polymeric biguanide to adjuvant is from 1:1 to 2:1.

Further improvements in the efficacy of the present method may be achieved by adding the adjuvant and polymeric biguanide to the recirculating water system in conjunction with one or more further antimicrobial compound(s). The addition of further antimicrobial compound(s) to the recirculating water system can provide a broader spectrum of antimicrobial activity and/or provide increased efficacy against particularly problematic algae, bacteria, yeast and/or fungi present in the recirculating water system. Furthermore, the combination of the adjuvant compound the polymeric biguanide and one or more further antimicrobial compound(s) may provide a synergistic effect.

The further antimicrobial compound(s) may possess antibacterial, anti-fungal, anti-algal or other antimicrobial activity. Suitable further anti-microbial compounds include agricultural fungicides, agricultural herbicides, algicides, sanitises, disinfectants or quaternary ammonium compounds and combinations thereof.

When the further antimicrobial compound is a sanitising agent the choice of sanitising agent will depend upon the recirculating water system in which it will be used. For recreational waters, suitable sanitising agents include for example chlorine, bromine, ozone, hydrogen peroxide, calcium hypochlorite, sodium hypochlorite, lithium hypochlorite, a chlorine release agent (preferably a chlorinated isocyanurate, or a chlorinated hydantoin, more preferably dichlorocyanuric acid or trichlorocyanuric acid), a bromine release agent, a hydrogen peroxide release agent, an ozone release agent or water-soluble copper or silver or chelated copper salts, (e.g. copper sulphate, chelated copper sulphate). In industrial recirculating water systems where the toxicity of the sanitising agent is not so important, other sanitisers may also be suitable for example 2-methylisothiazolinone, 5-chloro-2-methylisothiazolinone, benzisothiazolinone, 2-bromo-2-nitropropane-1,3-1,2-dibromo-2,4-dicyanobutane, methylene bisthiocyanate, 2-(thiocyanomethylthio)-benzothiazole, formaldehyde and formaldehyde release agents, glutaraldehyde, dibromonitrilopropionamide and bromo-hydroxyacetophenone or mixtures thereof.

When the further antimicrobial compound is a quaternary ammonium compound it may be a compound with a single quaternary ammonium group or a polyquaternary ammonium compound. Examples of suitable quaternary ammonium compounds include for example, N,N-diethyl-N-dodecyl-N-benzylammonium chloride, N,N-dimethyl-N-octadecyl-N-(dimethylbenzyl)ammonium chloride, N,N-dimethyl-N,N-didecylammonium chloride, N,N-dimethyl-N,N-didodecylammonium chloride; N,N,N-trimethyl-N-tetradecylammonium chloride, N-benzyl-N,N-dimethyl-N-($C_{12}$–$C_{18}$alkyl)ammonium chloride, N-(dichlorobenzyl)-N,-N-dimethyl-N-dodecylammonium chloride, N-hexadecylpyridinium chloride, N-hexadecylpyridinium bromide, N-hexadecyl-N,N,N-trimethylammonium bromide, N-dodecylpyridinium chloride, N-dodecylpyridinium bisulphate, N-benzyl-N-dodecyl-N, N-bis(beta-hydroxyethyl)ammonium chloride, N-dodecyl-N-benzyl-N, N-dimethylammonium chloride, N-benzyl-N,N-dimethyl-N-($C_{12}$–$C_{18}$ alkyl) ammonium chloride, N-dodecyl-N, N-dimethyl-N-ethylammonium ethylsulphate, N-dodecyl-N,N-dimethyl-N-(1-naphthylmethyl)ammonium chloride, N-hexadecyl-N,N-dimethyl-N-benzylammonium chloride or N-dodecyl-N,N-dimethyl-N-benzylammonium chloride.

In a preferred embodiment the further antimicrobial compound is a polyquaternary ammonium compound. Antimicrobial polyquaternary ammonium compounds which may be used include those described in U.S. Pat. Nos. 3,874,870, 3,931,319, 4,027,020, 4,089,977, 4,111,679, 4,506,081, 4,581,058, 4,778,813, 4,970,211, 5,051,124, 5,093,078, 5,142,002 and 5,128,100 which are incorporated herein by reference thereto.

Especially preferred polyquaternary compounds comprise a repeat unit of the Formula (7):

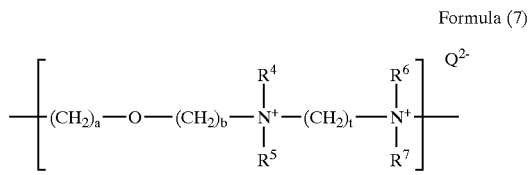

Formula (7)

wherein:

$R^4$, $R^5$, $R^6$ and $R^7$ each independently is $C_{1-6}$-alkyl optionally substituted by hydroxy;

$Q^{2-}$ is a divalent counter ion, two monovalent counter ions or a fraction of a polyvalent counter ion sufficient to balance the cationic charge in the repeat unit; and a, b and t each independently is 1 to 4.

Preferably $Q^{2-}$ is two monovalent anions selected from a halide anion and a trihalide anion, more preferably chloride or bromide.

$R^4$, $R^5$, $R^6$ and $R^7$ are preferably each independently $C_{1-4}$-alkyl, more preferably methyl.

a, b and t are preferably each independently 1, 2 or 3. It is especially preferred that a, b and t are 2.

The polyquaternary ammonium compound with the repeat unit of Formula (7) preferably has a average molecular weight of from 1,000 to 5,000. An especially preferred polyquaternary ammonium compound with a repeat unit of Formula (7) is poly(oxyethylene-(dimethyliminio)ethylene (dimethyliminio)ethylenedichloride). This polymer is commercially available under the Trademark WSCP from Buckman Laboratories Inc.

We have found that the use of a polyquaternary ammonium (especially poly(oxyethylene-(dimethyliminio)ethylene(dimethyliminio)ethylene dichloride)) in addition to the polymeric biguanide and adjuvant provides good protection against the growth of algae, especially those commonly found in recreational waters such as swimming pools. This combination is particularly useful as a remedial treatment for algal blooms in recreational waters.

When the further antimicrobial compound is a polyquaternary ammonium compound it is convenient to add the adjuvant and polyquaternary ammonium compound to the recirculating water system together as a formulation. Such formulations are commercially available, for example Busan 20/20™ (ex Buckman Laboratories Inc.) is a formulation comprising poly(oxyethylene-(dimethyliminio)ethylene (dimethyliminio)ethylene dichloride) and a salt of dodecylamine.

Alternatively, the further antimicrobial compound may be added to the recirculating water system together with the adjuvant and polymeric biguanide together as a composition comprising optionally a carrier. The carrier, when present, may be a solid or a liquid medium. Suitable solid and liquid carriers which may be employed are as previously described. When a further antimicrobial compound is present in such a composition, the further antimicrobial compound typically comprises from 5 to 50%, and preferably from 10 to 30% by weight of the composition.

The Recirculating Water System

The invention is applicable to any industrial or recreational recirculating water system but is especially suitable for recreational recirculating water systems. Examples of industrial water systems include heating and cooling systems, e.g. cooling towers and domestic central heating systems. Examples of recreational recirculating water systems include swimming pools, spas and ornamental ponds. The invention is also applicable to plumbing, pipework and other surfaces which form part of the industrial or recreational recirculating water systems and which are susceptible to infection by microorganisms.

Bext Mode

A preferred embodiment comprises a method for inhibiting the growth of or killing microorganisms, particularly algae, bacteria, yeast, and/or fungi in a recirculating water system, preferably a recreational recirculating water system, comprising adding to the water in either order or simultaneously:

(i) dodecylamine or a salt thereof; and
(ii) a polymeric biguanide, especially PHMB;

wherein the dodecylamine adjuvant is added to the water system to give a concentration thereof of from 0.1 to 24 ppm, preferably 0.5 to 15 ppm, more preferably 6 to 15 ppm and especially 6 to 10 ppm, and the polymeric biguanide is added to the water system to give a concentration thereof of from 1 to 20 ppm, preferably 5 to 12 ppm more preferably 6 to 10 ppm.

The combination of components (i) and (ii) provides very effective protection against the growth of microorganisms such as bacteria and "nuisance" algae, yeast and/or fungi without affecting water quality, especially water clarity.

Recirculating Water Systems

According to a second aspect of the present invention there is provided a recirculating water system comprising (i) water, an adjuvant of the Formula (1) as hereinbefore defined and a polymeric biguanide; and (ii) a means for recirculating the water; wherein the adjuvant and polymeric biguanide are dissolved in the water.

The preferred adjuvant and polymeric biguanide, their preferred amounts and the preferred water systems are as defined above in relation to the first aspect of the present invention.

The preferred means for recirculating the water comprises a pump.

Composition

According to a third aspect of the present invention there is provided a composition comprising:

(i) an adjuvant of the Formula (1) as hereinbefore defined;
(ii) a polymeric biguanide; and
(iii) optionally a carrier.

The preferred adjuvants, polymeric biguanides and carriers, and weight ratio of polymeric biguanide: adjuvant are as hereinbefore described in relation to the first aspect of the present invention.

In a preferred embodiment of the invention the composition comprises:

(a) from 10 to 60 parts of a mixture comprising the compound of Formula (1) and a polymeric biguanide; and (b) from 40 to 90 parts of a carrier wherein the parts (a) and (b) are by weight and the sum of the parts (a) and (b)=100.
Preferably the compositions comprises:
(a) from 5 to 30, more preferably 10 to 20 weight % of the compound of Formula (1) and from 5 to 30, more preferably 10 to 20 weight % of polymeric biguanide; and
(b) from 90 to 60 more preferably 80 to 40 weight % of carrier.

The compositions may be used to treat recirculating water systems, for example industrial and recreational recirculating water systems.

Kits

According to a fourth aspect of the present invention there is provided a kit for treating recirculating water comprising:
(i) an adjuvant of the Formula (1) as hereinbefore defined;
(ii) a polymeric biguanide; and
(iii) instructions for adding (i) and (ii) to a recirculating water system, preferably to a swimming pool, spa or ornamental pond. The instructions preferably comprise instructions to use (i) and (ii) for inhibiting the growth of and/or killing microorganisms such as algae, bacteria, yeast and/or fungi.

The invention is further illustrated by the following examples in which all parts and percentages are by weight unless otherwise indicated.

EXAMPLES 1 to 6

Preventative Laboratory Studies on Algae
Pre-Amble

Preventative treatments, as the name implies, are intended to prevent an outbreak occurring. Without adequate control measures, outbreaks can occur in two different scenarios. In the first scenario, the organism is present at all times but the concentration of the organism is so low that it is not noticeable. If a triggering event occurs, the organism reproduces rapidly resulting in a "bloom". Examples of triggering events are pH shifts, disturbance of a harbouring biofilm in the filter or plumbing, and introduction of additional but previously limited nutrients, such as nitrogen.

In the second scenario, low numbers of organisms can be introduced into a previously non-colonized pool that having optimal growth conditions. The combination of organisms and optimal growth conditions can result in a "bloom". The organisms can be introduced by the fill water, atmospheric dust, rainfall, or by bathing suits which have been previously used in infected pools or rivers and not washed before re-use.

In preventative laboratory treatment studies, growth conditions are optimised to support a bloom. An experimental flask is prepared with a medium having optimised growth conditions to support a bloom, the medium in the flask is treated with a prescribed concentration of a test formulation, and then inoculated with a low concentration of a bloom-forming organism. The medium is monitored for a period of time to observe whether the formulation is effective at preventing an algal bloom.

These studies used the most problematic organisms, i.e. field isolated mustard algae. Any compound that shows good efficacy against such organisms would be expected to provide even better control against the less environmentally-robust green and black algae.

Experimental

A series of innocula of naturally occurring mustard algae was prepared by inoculating flasks of modified Jaworski's medium with un-purified wild algal isolates collected in the field and containing low levels of bacteria and culturing the flasks for two weeks. The Jawaorski's medium was modified by the addition of 4 ppm polyhexamethylene biguanide (PHMB) (ex Avecia Inc.) to inhibit the growth of the bacteria present in the algal isolates. The inocula were harvested by aseptic vacuum filtration and the concentration of algal cell masses were combined ("pooled") and redispersed in a aseptic medium to provide a concentrated pooled inoculum. The amount of inoculum used was varied to achieve an initial optical density of 0.010 in the test flasks. The optical density was determined using a Milton Roy Spec 20 spectrophotometer.

Test adjuvants and Busan 20/20™ (ex Buckman Laboratories Inc. a mixture of dodecylamine and a polyquaternary ammonium compound (WSCP™)) were assessed, in triplicate, for anti-algal activity and a blank control, by adding each adjuvant or known Busan 20/20™ at 0 ppm and 15 ppm to Jaworski's medium (50 ml) contained in 125 ml flasks containing 6 mm borosilicate beads (50). Each flask was then inoculated with a prescribed amount of the pooled inoculum, so that the liquid in the flask had no visible green cast. The flasks (including a control or blank containing no adjuvant or Busan 20/20™ were closed with translucent caps and incubated at 80 F. for 10 days with 18 hours/day of illumination by a combination of fluorescent grow lamps and standard incandescent lamps. The incubation time was 10 days. Growth was scored by visual observation on a 0–4 scale and the results are shown in Table 1 below. A score of "1" indicates that the flask is slightly green. A score of "2" indicates that bloom has begun. A score of "4" indicates that the flasks are too turbid to see through. Any score >1 is considered a preventative failure.

TABLE 1

Visual score - Preventive Algae Control

| Example | Adjuvant | Adjuvant Conc. (ppm) | PHMB Conc. (ppm) | Average Visual Score | Comments |
| --- | --- | --- | --- | --- | --- |
| 1 | Dodecylamine | 2.5 | 4.0 | 0 | no visible growth |
| 2 | Dodecylamine | 5.0 | 4.0 | 0 | no visible growth |
| 3 | Dodecylamine | 10.0 | 4.0 | 0 | no visible growth |
| 4 | Dodecylamine | 15.0 | 4.0 | 0 | no visible growth |
| 5 | Busan 20/20 ™ | 10.0 | 4.0 | 0 | no visible growth |
| 6 | Busan 20/20 ™ | 15.0 | 4.0 | 0 | no visible growth |
| Control | None | 0 | 4.0 | 4.0 | very heavy growth |
| Control | None | 0 | 0 | 4.0 | very heavy growth |

The data in Table 1 clearly illustrates the effectiveness of the combinations of PHMB and dodecylamine and PHMB and Busan 20/20™ over the PHMB, alone, at preventing the field isolated mustard algae outbreak from occurring.

EXAMPLES 7 to 12

Remedial Laboratory Studies on Algae Pre-Amble

Remedial treatments are intended to reduce a bloom of algae once it has already occurred. During blooms the algal infestation of the system is obvious, even to the casual observer. Effective remedial treatments are those that reduce the obvious symptoms, even if they do not result in a complete kill of the algae. Remedial treatments are considered effective if they return the system to a pre-bloom state.

Remedial efficacy was evaluated in this example using field isolated mustard algae. Any treatment showing good control of this organism is expected to display similar efficacy against green and black algae.

Experimental

Studies were conducted in 125 ml flasks containing 6 mm borosilicate glass beads (50) and Jaworski's medium (50 ml). The flasks were inoculated with pooled cultures of mustard algae to achieve an initial absorbance of 0.10, as measured using a Milton Roy Spec 20 Spectrophotometer. This concentration of algae in the water resulted in a noticeable green colour similar to that seen after brushing pools with moderate blooms. The adjuvants identified in Table 2 were added at levels of 1.25 and 2.5 ppm active ingredient. Busan 20/20™ identified in Table 3 was added at levels of 0.625, 1.25, 2.5 and 5.0 ppm. The performance of the adjuvants were compared to the controls with and without PHMB. The flasks were closed using translucent caps, illuminated for 8 hours using a combination of fluorescent grow lamps and standard incandescent lamps each day and incubated at 80° F. for a period of 5 days. Algal growth was measured after 5 days using a Milton Roy Spec 20 spectrophotometer. The higher the optical density the heavier the growth. Treatments that result in a terminal optical density of less than 0.2 display either algistatic or algicidal activity. The results are shown in Table 2.

TABLE 2

Remedial Algae Control

| Example | Adjuvant | Adjuvant Conc. (ppm) | PHMB Conc. (ppm) | Average Optical Density | Comments |
|---|---|---|---|---|---|
| 7 | Dodecylamine (Armeen 12D ™) | 2.5 | 4.0 | 0.12 | Control |
| 8 | Dodecylamine (Armeen 12D ™) | 1.25 | 4.0 | 0.08 | Excellent Control |
| 9 | Octadecyl-amine (Armeen 18 D ™) | 2.5 | 4.0 | 0.08 | Excellent Control |
| 10 | Octadecyl-amine (Armeen 18 D ™) | 1.25 | 4.0 | 0.16 | Control |
| 11 | Dimethyl-octadecylamine (Armeen DM 18D ™) | 2.5 | 4.0 | 0.07 | Excellent Control |
| 12 | Dimethyl-octadecylamine (Armeen DM 18D) | 1.25 | 4.0 | 0.12 | Control |
| Control | None | 0 | 4.0 | 0.62 | Very heavy growth |
| Control | None | 0 | 0 | 0.48 | Heavy growth |

Footnote to Table 2: Armeen 12D, Armeen 18D and Armeen DM are trademark names for dodecylamine, octadecylamine and dimethyloctadecylamine ex Akzo Nobel.

The data in Table 2 shows that all of the combinations of adjuvants and PHMB were successful at significantly reducing the growth of the field isolated mustard algae and much more effective than the PHMB by itself. Also, there was no significant difference in the performance of the straight chained octadecylamine and dimethyloctadecylamine at 2.5 ppm.

EXAMPLE 13

Effect of an Additional Polyguaternary Ammonium Compound on the Control of Algal Growth The experiments described in Examples 7 to 9 were repeated except that in place of the dodecylamine Busan 20/20™ (a mixture of dodecylamine and a polyquaternary ammonium compound available under the trademark WSCP ex Buckman Laboratories Inc.) was used. The results are shown in Table 3.

TABLE 3

Remedial Algae Control

| Example | Adjuvant | Conc (ppm) | PHMB Conc. (ppm) | Average Optical Density | Comments |
|---|---|---|---|---|---|
| 13 | Busan 20/20 ™ | 0.625 | 4.0 | 0.32 | Moderate growth |
| 14 | Busan 20/20 ™ | 1.25 | 4.0 | 0.20 | Slight growth |
| 15 | Busan 20/20 ™ | 2.5 | 4.0 | 0.16 | Control |
| 16 | Busan 20/20 ™ | 5.0 | 4.0 | 0.12 | Control |
| Control | None | 0 | 4.0 | 0.81 | Very heavy growth |
| Control | None | 0 | 0 | 0.51 | Heavy growth |

The data in Table 3 shows that at concentrations of Busan 20/20™ greater than or equal to 1.25 ppm in combination with PHMB gave a significant improvement over PHMB alone.

EXAMPLE 17

Effect of Adjuvant on Water Clarity

When treating recreational waters such as swimming pools or spas it is highly desirable to add an agent to the water which can be dosed in one application or will accumulate over time and will not adversely effect the water quality, for example clarity, colour, foaminess, or objectionable odour or taste. If swimming pool water is not clear it could present a hazard to swimmers who may not be able to see the pool's sides or bottom.

Experimental

Six 10 gallon fish aquariums equipped with a heater and a recirculating pump (to simulate a swimming pool environment) were filled with simulated swimming pool water containing polyhexamethylene biguanide (PHMB) comprising:

| | |
|---|---|
| Sodium bicarbonate (total alkalinity) | 80–150 ppm |
| Calcium chloride (hardness) | 180–275 ppm |
| Hydrogen peroxide | 25–30 ppm |
| Polyhexamethylene biguanide (PHMB) | 6–12 ppm |

To these tanks was added the adjuvant shown in Table 4. The pH of the tanks was maintained between 7.2 and 7.8 and the water temperature was maintained at 70±3° F. After the chemical additions the water was circulated for 24 hours. The water in each tank was then visually inspected and tested for turbidity using a Hach Turbidimeter. The results are shown in Table 4.

TABLE 4

Effect of Dodecylamine and Tetradecylamine on Water Clarity

| Tank | Adjuvant | Adjuvant Concentration (ppm) | Turbidity (NTU) | Visual Observations |
|---|---|---|---|---|
| 1 | Control | 0 | 2.3 | Clear |
| 2 | Dodecylamine | 2.5 | 2.7 | Clear |
| 3 | Dodecylamine | 5.0 | 1.8 | Clear |
| 4 | Dodecylamine | 10.0 | 2.5 | Clear |
| 5 | Tetradecylamine | 5.0 | 10.1 | Cloudy |
| 6 | Tetradecylamine | 10.0 | 19.0 | Cloudy |

The results in Table 4 clearly indicate that the dodecylamine had no effect on water clarity whereas tetradecylamine resulted in water turbidity.

What is claimed is:

1. A recirculating water system comprising:
(i) water,
an adjuvant selected from the group consisting of dodecylamine and salt thereof,
a polyquaternary ammonium compound comprising a repeat unit of the formula:

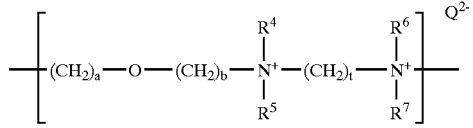

Formula wherein:
$R^4$, $R^5$, $R^6$ and $R^7$ each independently is $C_{1-6}$-alkyl optionally substituted by hydroxy;
$Q^{2-}$ is a divalent counter ion, two monovalent counter ions or a fraction of a polyvalent counter ion sufficient to balance the cationic charge in the repeat unit; and
a, b and t each independently is 1 to 4; and
polymeric biguanide; and
(ii) a means for recirculating (i); wherein the adjuvant, polyquaternary ammonium compound and polymeric biguanide are dissolved in the water and wherein the adjuvant, polyquaternary ammonium compound, and polymeric biguanide are present in an amount effective in inhibiting the growth of or killing algae, bacteria, and/or fungi in the recirculating water system without affecting water clarity.

2. A recirculating water system according to claim 1 comprising water, polyhexamethylene biguanide hydrochloride salt PHMB as the polymeric biguanide and poly(oxyethylene-(dimethyliminio)ethylene (dimethyliminio)ethylene-dichloride as the polyquaternary ammonium compound and wherein dodecylamine or salt thereof is included in the water system at a concentration thereof of from 0.1 to 24 ppm and the PHMB is present in the water system at a concentration thereof of from 1 to 20 ppm.

3. A kit for treating recirculating water comprising
(i) an adjuvant selected from the group consisting of dodecylamine and salt thereof,
(ii) a polyquaternary ammonium compound comprising a repeat unit of the formula:

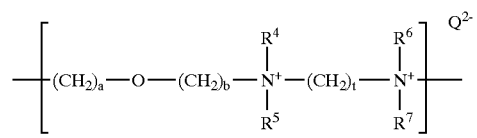

Formula wherein:
$R^4$, $R^5$, $R^6$ and $R^7$ each independently is $C_{1-6}$-alkyl optionally substituted by hydroxy;
$Q^{2-}$ is a divalent counter ion, two monovalent counter ions or a fraction of a polyvalent counter ion sufficient to balance the cationic charge in the repeat unit; and
a, b and t each independently is 1 to 4;
(iii) a polymeric biguanide; and
(iv) instructions for adding (i), (ii) and (iii) to a recirculating water system, the adjuvant, polyquaternary ammonium compound, and polymeric biguanide being present in an amount effective in inhibiting the growth of or killing algae, bacteria, and/or fungi, in a recirculating water system without affecting water clarity.

4. A system according to claim 1 or a kit according to claim 3 wherein the polyquaternary ammonium compound is poly(oxyethylene-(dimethylimino)ethylene (dimethylimino)ethylene-dichloride.

5. A composition comprising (i) an adjuvant selected from the group consisting of dodecylamine and salt thereof, (ii) a polyquaternary ammonium compound comprising a repeat unit of the formula:.

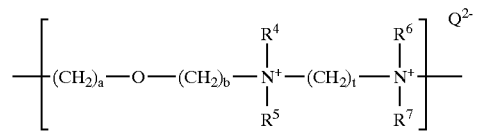

Formula wherein:
$R^4$, $R^5$, $R^6$ and $R^7$ each independently is $C_{1-6}$-alkyl optionally substituted by hydroxy;
$Q^{2-}$ is a divalent counter ion, two monovalent counter ions or a fraction of a polyvalent counter ion sufficient to balance the cationic charge in the repeat unit; and
a, b and t each independently is 1 to 4; and
(iii) a polymeric biguanide, the adjuvant, polyquaternary ammonium compound, and polymeric biguanide being present in an amount effective in inhibiting the growth of or killing algae, bacteria, and/or fungi, in a recirculating water system without affecting water clarity.

6. A composition according to claim 5 wherein the weight ratio of adjuvant to polymeric biguanide is 99:1 to 1:99.

7. A composition according to claim 6 wherein the weight ratio of adjuvant to polymeric biguanide is 1:2 to 2:1.

8. A composition according to claim 6 wherein the weight ratio of adjuvant to polymeric biguanide is from 4:1 to 1:4.

9. A composition according to claim 8 wherein the weight ratio of adjuvant to polymeric biguanide is from 1:1 to 2:1.

10. A composition according to claim 5 which further comprises a carrier.

11. A composition according to claim 10 which comprises:
 (a) from 10 to 60 parts of said adjuvant, and a polymeric biguanide; for
 (b) from 40 to 90 parts of a carrier.

12. A composition according to claim 11 which comprises:
 (a) from 5 to 30 weight % of said adjuvant, from 5 to 30 weight % polymeric biguanide; from 5 to 50 weight % of said polyquaternary ammonium compound; and
 (b) from 90 to 60 weight % carrier.

13. A composition according to claim 12 wherein the carrier comprises a water miscible organic solvent.

14. A composition according to claim 12 wherein the polyquaternary ammonium compound comprises from 10 to 20% by weight of the composition.

15. A composition according to claim 5 wherein the polyquaternary ammonium compound is poly(oxyethylene-(dimethylimino)ethylene (dimethylimino)ethylene-dichloride.

* * * * *